United States Patent [19]

MacGregor

[11] Patent Number: 4,458,366
[45] Date of Patent: Jul. 10, 1984

[54] ARTIFICIAL IMPLANTABLE BLOOD PUMP

[76] Inventor: David C. MacGregor, 81 Wimbleton Rd., Islington, Ontario, Canada

[21] Appl. No.: 405,763

[22] Filed: Aug. 6, 1982

Related U.S. Application Data

[63] Continuation of Ser. No. 157,952, Jun. 9, 1980, abandoned, which is a continuation-in-part of Ser. No. 824,296, Aug. 15, 1977, Pat. No. 4,280,514, which is a continuation-in-part of Ser. No. 683,382, May 5, 1976, Pat. No. 4,101,984.

[51] Int. Cl.$^3$ .................... A61F 1/24; A61F 1/00
[52] U.S. Cl. .................................. 3/1.7; 3/1; 3/1.4; 128/1 D
[58] Field of Search ............ 3/1, 1.4, 1.5, 1.7; 128/1 D

[56] References Cited

U.S. PATENT DOCUMENTS

| | | | |
|---|---|---|---|
| 3,568,214 | 3/1971 | Goldschmied | 3/1.7 |
| 3,608,088 | 9/1971 | Dorman et al. | 3/1.7 |
| 3,700,380 | 10/1972 | Kitrilakis | 3/1 |
| 3,755,825 | 9/1973 | DeBakey et al. | 3/1.7 |
| 3,855,638 | 12/1974 | Pilliar | 3/1 |
| 4,011,861 | 3/1977 | Enger | 3/1 X |
| 4,017,911 | 4/1977 | Kafesjian et al. | 3/1.5 |
| 4,044,404 | 8/1977 | Martin et al. | 3/1.7 |

OTHER PUBLICATIONS

"Use of the Computer to Monitor Long-Term Cardiac Assistance", by T. H. Stanley et al., The Journal of Thoracic & Cardiovascular Surgery, vol. 57, No. 4, Apr. 1969, pp. 519-526.

"Thrombus Generation Within the Artificial Heart", by D. B. Olsen et al., The Journal of Thoracic & Cardiovascular Surgery, vol. 70, No. 2, Aug. 1975, pp. 248-255.

"Prolonged Pulsatile and Nonpulsatile LV Bypass with Centrifugal Pump", by G. G. Johnston et al., Transactions American Soc. Artif. Internal Organs, vol. XXII, Apr. 1976, pp. 323-331.

*Primary Examiner*—Ronald L. Frinks
*Attorney, Agent, or Firm*—Sim & McBurney

[57] ABSTRACT

Implantable artificial blood pumps are described. The blood-contacting surfaces have pores therein which communicate with a subsurface of interconnected pores. This structure induces tissue formation thereon and avoidance of the incidence of thromboembolism.

15 Claims, 10 Drawing Figures

ARTIFICIAL IMPLANTABLE BLOOD PUMP

REFERENCE TO RELATED APPLICATIONS

This is a continuation of application Ser. No. 157,952 filed June 9, 1980, now abandoned, which is a continuation-in-part of U.S. patent application Ser. No. 824,296 filed Aug. 15, 1977 (now U.S. Pat. No. 4,280,514) which is a continuation-in-part of U.S. patent application Ser. No. 683,382 filed May 5, 1976 (now U.S. Pat. No. 4,101,984).

FIELD OF INVENTION

The present invention relates to artificial implantable blood pumps.

BACKGROUND OF THE INVENTION

It is well known that the introduction of foreign bodies in the blood stream, such as, polished metal surfaces in artificial blood pumps, tends to cause the formation of blood clots which may break loose and embolize to various parts of the body.

SUMMARY OF THE INVENTION

The present invention provides an artificial blood pump structure wherein blood-contacting surfaces are rendered resistant to the formation of blood clots normally associated with the presence of foreign bodies in the blood stream. In the devices of the invention, the blood-contacting surfaces are porous and are in fluid flow communication with a network of interconnected interstitial pores below the surface.

The provision of the porous surface and subsurface network promotes the formation of a smooth thin adherent tissue coating on the porous surface. The tissue is formed by colonization of nucleated cells circulating in the blood stream onto the porous surface and subsequent differentiation into other cell types. The tissue coating organizes over about a one to three month period, does not appear to increase significantly in thickness thereafter and includes flattened endothelial-like cells at the surface thereof.

DESCRIPTION OF PREFERRED EMBODIMENTS

Referring first to FIGS. 1 to 8, there is illustrated therein an artificial blood pump 10 including a part-spherical rigid housing 12. Mounted in a cavity 14 in the housing is a resiliently flexible diaphragm 16 which defines with the adjacent inner housing walls a working volume 18 which varies with the position of the diaphragm 16.

Figure 1:
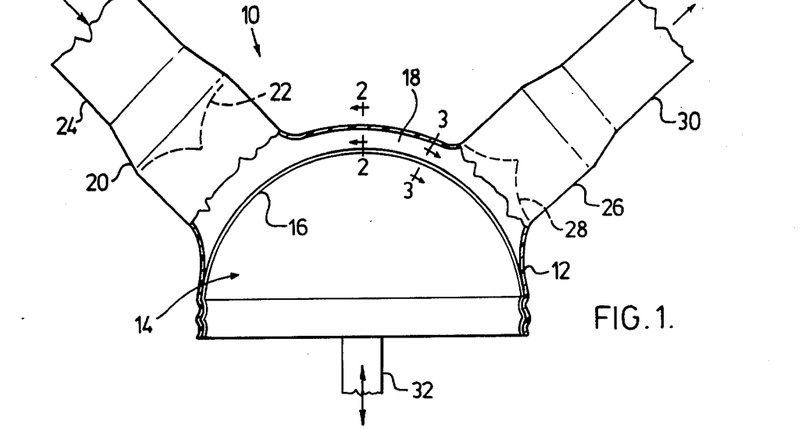
FIG. 1 is a part-sectional schematic view of an artificial blood pump constructed in accordance with one preferred embodiment of the invention.

An inlet conduit 20 having a one-way valve 22 mounted therein communicates with the working volume 18 of the cavity 14 through the wall of the housing 12 to establish fluid flow communication between a blood vessel 24 and the working volume 18.

An outlet conduit 26 having a one-way valve 28 mounted therein also communicates with the working volume 18 of the cavity 14 through the wall of the housing 12 to establish fluid flow communication between a blood vessel 30 and the working volume 18.

The one-way valve 20 is arranged to permit blood to flow from the vessel 24 into the housing 12 and not vice-versa while the one-way valve 28 is arranged to permit blood to flow from the housing 12 to the vessel 30 and not vice-versa.

The side of the diaphragm 16 opposite to the working volume 18 within the cavity 4 communicates with a source of pressure (not shown) through pipe 32 to effect actuation of the diaphragm 16. In FIG. 1, the diaphragm 16 is shown at its stretched location with pressure being applied through pipe 32.

In operation, relaxing of the diaphragm 16 by removal of the pressure causes the resiliently flexible diaphragm 16 to contract so that the working volume 18 of the cavity 14 increases. The suction resulting thereby closes the outlet valve 28 and opens the inlet valve 22 thereby drawing blood into the increasing working volume 18 of the cavity 14 from the vessel 24. When the resiliently flexible diaphragm 16 reaches its retracted position, pressure is once again applied thereto through pipe 32, expanding the same and causing the working volume 18 of the cavity 14 to decrease. The pressure resulting thereby closes the inlet valve 22 and opens the outlet valve 28 thereby pumping blood out of the decreasing working volume 18 of the cavity 14 into the vessel 30.

The cyclic operation of drawing blood into the pump 10 through valve 22 and expelling blood from the pump 10 through valve 28 is repeated on a regular basis and some form of timing mechanism is used to control the repetitive application and relaxation of pressure. The blood pump 10 is sized and the frequency of the cyclic operation is controlled to provide a blood throughput from the blood vessel 24 to the blood vessel 30 of about 1 to about 30 liters of blood per minute, preferably about 5 liters per minute.

Figures 2, 6:
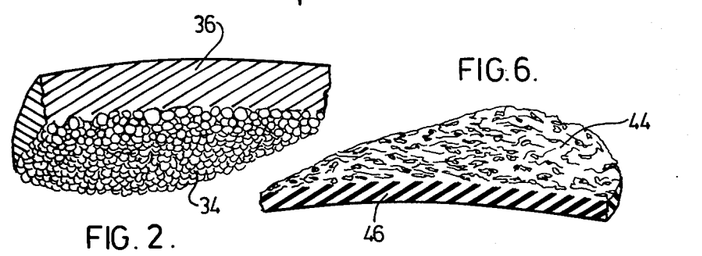
FIG. 2 is an enlarged sectional view taken on line 2—2 of FIG. 1 and line 2—2 of FIG. 9.
FIG. 6 is an enlarged sectional view taken on line 3—3 of FIG. 1.
Figure 3:
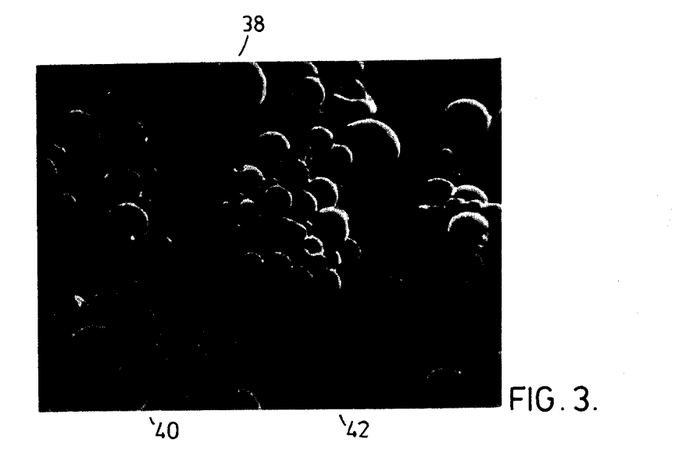
FIGS. 3 and 4 are respectively low (x600) and high (x3000) power scanning electron micrographs of the porous metal surface shown in FIG. 2.
Figure 4:
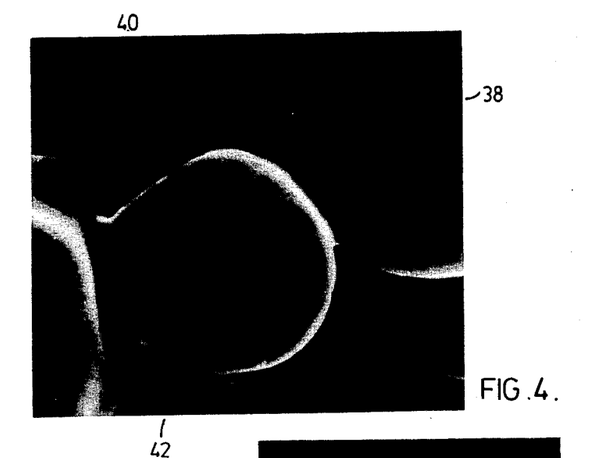

As may be seen from the enlarged sectional view of FIG. 2 and the low (x600) and high (x3000) power scanning electron micrographs of FIGS. 3 and 4, the rigid housing 12 is constructed with an internal porous surface region 34 which engages the blood in the working volume 18 and a dense coherent substrate region 36. The material of construction of the rigid housing 12 usually is a biocompatible metal or biocompatible rigid polymeric material. The term "metal" is used herein includes pure metals and alloys of two or more metals. The porous internal surface region 34 and the dense substrate region 36 often are constructed of the same material for ease of fabrication, although different materials may be used for the two regions.

In the structure illustrated, the housing 12 is constructed of metal and the porous internal surface region 34, adhering to the dense substrate region 36, consists of a plurality of metal particles 38 joined together to form surface pores 40 and an interconnected network of subsurface pores 42 communicating with the surface pores 40 and substantially uniformly distributed throughout the surface region 34.

Figure 5:
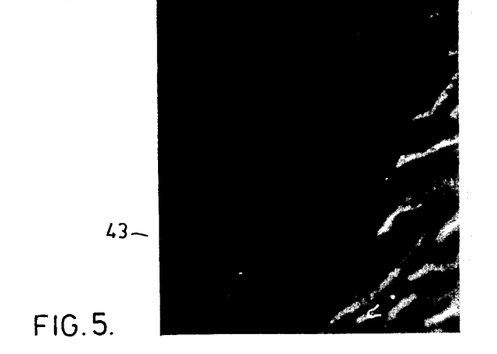
FIG. 5 is a scanning electron micrograph of tissue covering the porous metal surface of FIG. 2 following implantation.

The porous internal surface region 34 engages blood flowing through the working volume 18 of the cavity 14 and promotes the colonization of nucleated cells thereon. The colonized cells subsequently differentiate into other cell types and form a tissue coating. This tissue coating grows on the surface and through the surface pores 40 into the subsurface network of pores 42, interlocking with the pore network 42. The tissue organizes over about a one to three month period and does not appear to increase significantly in thickness thereafter. The scanning electron micrograph of FIG. 5 shows the form of the tissue coating 43 which is formed on the porous metal surface 34.

In this way, the blood passing through the working volume 18 is contacted by a tissue surface 43 rather than by a polished metal surface, so that the incidence of thromboembolism resulting from metal surfaces engaging the blood is minimized.

The porous internal surface region 34 usually has a thickness of less than about 500 microns, preferably about 25 to about 300 microns. The metal particles 38 forming the porous surface region 34 usually have a size of about −100 mesh. Preferably a mixture of particles of varying particle sizes within a narrow range of particle size is used, namely −100 +325 mesh, −325 +500 mesh or −500 mesh. The smaller particle size mixtures are preferred since these result in a smoother surface exposed to the blood, thereby minimizing blood turbulence during tissue formation.

The porous internal surface region 34 has a porosity of about 10 to about 50% by volume. The interface between the internal surface region 34 and the substrate region 36 and the porous surface region 34 itself both have a shear strength of greater than about 1000 psi to ensure adequate structural strength.

The substrate region 36 may have any desired thickness compatible with weight considerations and the necessity to provide adequate structural strength to withstand the pumping action effected within the housing 12.

The composite structure of the rigid coherent metal substrate region 36 and the porous metal surface region 34 may be formed by a sintering procedure, in which a multiple number of layers of adhered particles are simultaneously formed on the substrate.

The sintering procedure involves roughening the smooth coherent internal surface of the housing 12, forming a self-supporting coating of a plurality of layers of metallic particles bound together and to the substrate by a suitable adhesive, drying the binder to provide a preform of dried coating on the substrate, and sintering the preform to cause metal fusion interconnection of the metal particles one with another and with the roughened metal substrate.

In an alternative procedure, the preform may be formed from particles of a metal compound which is readily thermally decomposable, or a mixture of particles of such compounds, which thermally decompose during the sintering step and result in the interconnection of metal particles with each other and to the substrate. When this technique is used, irregularly-shaped particles and pores result rather than the regular substantially spherical shape of particles 38.

The precise sintering technique adopted depends to some extent on the size of the particles from which the porous surface region 34 is formed and whether the particles are in metal or metal compound form. The metal of the substrate region 36 and of the porous surface region 34 usually are the same, although different metals may be used, if desired.

As noted above, the metal and metal compound particles 38 from which the porous surface region 34 is formed generally fall into one of three categories, namely −500 mesh (less than about 20 microns), −325 +500 mesh (about 20 to about 50 microns), and −100 +325 mesh (about 50 to about 200 microns). The term "mesh" used herein refers to the U.S. Standard Sieve mesh size.

The initial roughening of the smooth coherent internal surface of the housing 12 may be carried out in any convenient manner, for example, by blasting with abrasive material. Thereafter, the coating of particles 38 is formed on the surface.

In one procedure, a binder for the particles 38 first is sprayed onto the roughened metal surface and the device then is suspended in a fluidized bed of powder metal particles 38 or powder metal compound particles to form a coating on the roughened surface. The coated body is withdrawn from the fluidized bed and the binder allowed to dry. This procedure has been found to be satisfactory for each of the particle sizes, except for the −500 mesh particles.

In an alternative procedure, the powder metal or metal compound particles are mixed with a binder to form a fairly viscous slurry which is spray applied to the roughened surface to form the coating thereon, the coating thereafter being dried. It has been found that this procedure is satisfactory for −325 mesh size particles.

In a further procedure, the metal or metal compound particles and binder are slurried and the roughened surface is dipped into the slurry. Excess material is allowed to run off and the coated body is dried.

Other methods of powder metal particle application may be adopted.

In each case, where the coating is formed from metal particles 38, after the formation of the dried coating on the substrate, the preform of dried coating and substrate is sintered to cause metal fusion interconnection of the metal particles one with another and with the roughened substrate surface to provide the rigid porous surface region 34 consisting of multiple layers of particles having a network of interconnected pores substantially uniformly distributed throughout and coated on the rigid substrate region 36.

It is possible to build up any desired thickness of porous coating on the coherent substrate by presintering the dried coating to provide some strength thereto and then repeating the coating and presintering operation for as many cycles as is required to build up the desired thickness. Each layer formed on the substrate contains a plurality of layers of particles. When the desired thickness has been achieved, the composite is sintered to provide the required particle-particle and particle-substrate bonds.

The presintering and sintering temperatures which are preferably utilized depend on the particle size of the metal particles, lower temperatures generally being used for smaller particle sizes.

Thus, for −500 mesh metal particles, presintering preferably is carried out by heating at a temperature of about 2000° F. (about 1100° C.) momentarily or up to about 10 minutes and then cooling. In this case, sintering preferably is carried out by heating at a temperature of about 2150° F. (about 1175° C.) for about 60 to about 90 minutes in a hydrogen or other reducing gas atmosphere, or under vacuum.

For the −325 +500 mesh metal particles, presintering preferably is carried out by heating at a temperature of about 2100° F. (about 1150° C.) for about 8 minutes, while sintering preferably is carried out by heating at a temperature of about 2200° F. (about 1200° C.) for about 60 to about 90 minutes in a hydrogen or other reducing gas atmosphere, or under vacuum.

When metal particles of particle size −100 +325 mesh are used, the presintering preferably is carried out at a temperature of about 2200° F. (about 1200° C.) and sintering preferably is carried out at a temperature of about 2200° to about 2300° F. (about 1200° C. to about 1250° C.) for about 2 to about 3 hours, in a hydrogen or other reducing gas atmosphere, or under vacuum.

In the case where the coating is formed from thermally-decomposable metal compound particles, the preform is heated to an elevated temperature to cause thermal decomposition of the metal compound and the formation of the rigid porous surface region 34 of pure metal particles which are connected together at their points of contact with each other and the substrate to define a network of interconnected pores substantially uniformly distributed throughout and coated on the rigid coherent substrate region 36.

The technique described above for the building up of layers of particles to the required thickness may be adopted. The presintering and sintering temperatures which are preferably utilized correspond generally to those for metal particles of the same size.

The use of metal compounds in the sintering process is especially beneficial in those instances where particles of the metal itself cannot be used at the desired particle size for any particular reason. For example, certain metals, such as titanium, are pyrophoric at small particle sizes.

Non-pyrophoric thermally-decomposable metal compounds, such as, the hydrides of those metals, then are used in place of the metal. Vacuum is usually used to withdraw the gas formed during the thermal decomposition of the metal compound.

Following formation of the porous surface region 34 utilizing the above techniques, the coating may be machined and refined, if desired, to improve its surface characteristics.

If desired, a porous surface may be provided on the external surface of the housing 12. A porous external surface permits the growth of soft body tissue therein, so as to achieve fixation of the blood pump 10 in the body, as described in more detail in my copending U.S. patent application Ser. No. 959,212 filed Nov. 9, 1978, now abandoned, the disclosure of which is incorporated herein by reference. Such a porous external surface may be of metal and of the same type as that described for the metal form of the internal surface region 34, or of polymeric material and of the same type as described below with respect to the surface region of the diaphragm 16.

Figure 7:
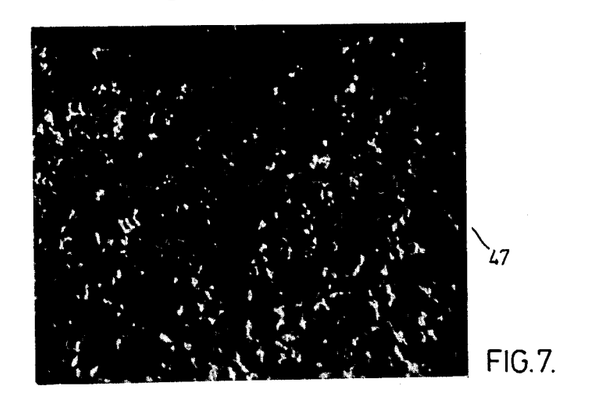
FIGS. 7 and 8 are respectively low (x100) and high (x2000) power scanning electron micrographs of the porous polymer surface shown in FIG. 6.
Figure 8:
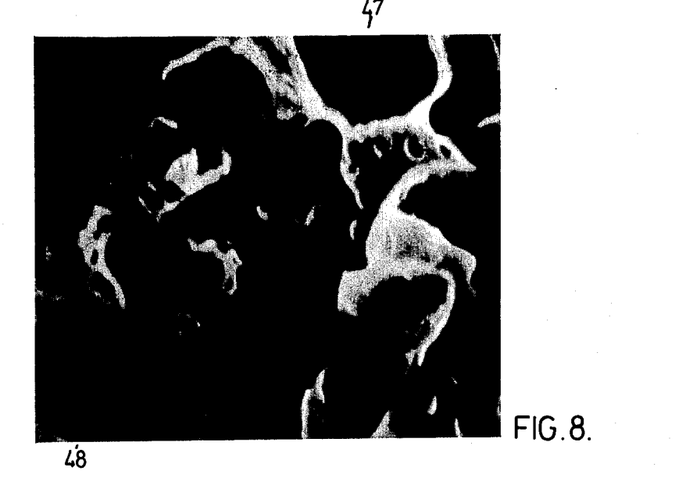

As may be seen from the enlarged sectional view of FIG. 6, and the low (x100) and high (x2000) power scanning electron micrographs of FIGS. 7 and 8, the resiliently flexible diaphragm 16 is constructed with a porous surface region 44 which engages the blood in the working volume 18 and a dense coherent substrate region 46. The material of construction of the resiliently flexible diaphragm 16 is a resiliently flexible biocompatible polymeric material.

The porous surface region 44 includes surface pores 47 and an interconnected network of pores 48 communicating with the surface pores 47 and substantially uniformly distributed throughout the surface region 44.

The porous surface region 44 engages blood flowing through the working volume 18 of the cavity 14. In the same way that tissue forms on the porous inner surface region 34 on the internal wall of the housing 12, a tissue surface forms on the porous surface region 44 of the diaphragm. Hence, all the blood-contacting surfaces of the working volume 18 of the cavity 14 are tissue covered, thereby avoiding the incidence of thromboembolism associated with the contact of foreign bodies with blood.

The wall thickness of the diaphragm 16 may vary widely but usually is about 0.2 to about 1.0 mm. The pore size of the pores 47 and the pores in the network 48 is less than about 200 microns, preferably less than about 50 microns and more preferably less than about 20 microns, while the porosity of the surface region 44 may vary from about 10 to about 70 vol.%.

The diaphragm 16 is required to have a minimum strength to prevent structural breakdown with use and hence should be able to withstand pulsatile arterial blood pressure of greater than about 300 mm Hg, preferably greater than about 500 mm Hg, for a prolonged period of time, generally greater than one year and preferably greater than about 5 years.

If desired, the diaphragm 16 may have reinforcement for the surface region 44, such as a layer of fabric bonded to or within the surface region 44.

The composite structure of the flexible polymeric substrate region 46 and the porous polymeric surface region 44 of the diaphragm 46 may be formed by a variety of procedures. As noted above, the housing 12 may be constructed of rigid polymeric material and techniques equivalent to those used to form the resiliently flexible diaphragm 16 may be used to form the housing 12, the major difference being in the polymeric material used, in the case of the diaphragm 16 flexibility being required and in the case of the housing 12 rigidity being required.

One preferred procedure for forming a porous polymeric structure is to uniformly disperse solvent-elutable particles in a continuous or discontinuous polymer phase, form a coherent shaped article from the dispersion wherein solvent-elutable particles are substantially uniformly dispersed throughout a continuous solid polymer phase in generally intraparticulate contact, and elute the solvent-elutable particles from the article to provide a porous shaped product having interconnected pores therein. The resulting porous structure is shown in the scanning electron micrographs of FIGS. 7 and 8.

The above-described porous polymer forming procedure may be effected in a number of different ways, the particular one chosen depending on the shape of product desired, the nature of the polymer used and the form of the product desired. One such procedure involves pulverizing a rigid polymer to the desired particle size, mixing the powder with the solvent-elutable particles, compressing the mixture, molding or extruding the mixture to the desired shape and leaching the solvent elutable particles from the coherent shaped article to remove the solvent-elutable particles.

Another specific procedure involves blending together a moldable and/or extrudable polymeric material and solvent-eludable particles in sufficient quantities to provide a continuous phase of polymer and a dispersed phase of solvent-elutable particles in the blend. Thereafter, the blend is molded or extruded to the desired shape and contacted with solvent to remove the solvent-elutable particles and leave an open network of interconnected pores throughout the body.

In a modification of this procedure, the polymer may be provided as a solution into which the solvent-elutable particles are mixed. After removal of the solvent, the molding or extruding and leaching operations are carried out.

Yet another specific procedure for forming the microporous polymer product involves initial formation of beads of polymer having a core of solvent-elutable material by polymer solution coating of the core material, compression molding or extruding of the beads to the desired shape and product leaching to remove the solvent-elutable material.

A further specific procedure for the formation of a microporous polymeric product includes forming a viscous casting solution of the polymer, dispersing the solvent-elutable particles in the solution, casting the solution onto a casting surface and, after removal of solvent, eluting the solvent-elutable particles from the cast material.

The porous polymeric structure formed by these procedures is laminated with one or more coherent solid polymer substrates. Such laminates may be formed by conventional techniques, using suitable bonding between the porous material and the substrate.

Where it is desired to provide reinforcement to the porous material, such as, by way of a knitted and/or woven fabric, as described above, such material may be incorporated into the structure by suitable modification to the porous structure-forming procedure.

The composite may also be formed by providing the solvent-elutable particles in part only of the shaped material and then eluting the particles from that part, forming a porous region in the eluted portion.

The cavity 12 also may be constructed with a coherent metal substrate region 36 and a porous polymer surface region 34. Such a structure may be provided by laminating a metal composite porous metal coated surface with a polymer composite porous polymer coated surface by causing the coherent portion of the polymer composite to flow into and harden within the pore network 42 of the metal composite.

The inlet conduit 20 and outlet conduit 26 are integrally formed with the housing 12 and usually are constructed in identical manner to the housing 12. The one-way inlet valve 22 and the one-way outlet valve 28 may be of any convenient construction and are preferably constructed as described in my U.S. Pat. No. 4,101,984, the disclosure of which is incorporated herein by reference.

The embodiment of the invention described above with respect to FIGS. 1 to 8 is an artificial blood pump 10 of superior construction to conventional artificial blood pumps in that blood-contacting surfaces of the blood pump 10 have tissue coatings therein which avoid prior art difficulties of thromboembolism.

The blood pumps of the type described above with respect to FIGS. 1 to 8 may be combined with an artificial heart for both the pulmonary and systolic sides of the circulation.

Figure 9:
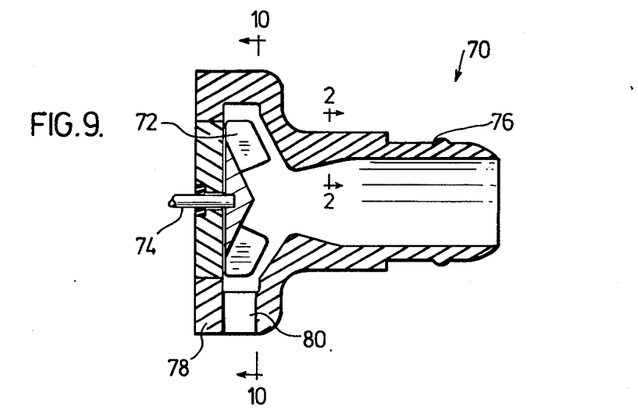
FIG. 9 is a sectional view of an artificial blood pump constructed in accordance with a second preferred emeobiment of the invention.
Figure 10:
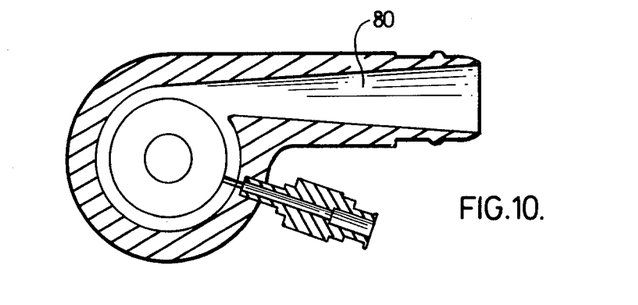
FIG. 10 is a sectional view taken on line 10—10 of FIG. 9.

In FIGS. 9 and 10, there is illustrated a blood pump 70 of different construction from that discussed above with respect to FIGS. 1 to 8. In this embodiment of the invention, in place of the valves and flexible diaphragm, an impeller 72 is used to effect motion of blood through the pump 70.

The impeller 72 is mounted on shaft 74 for rotation by a drive motor (not shown). An inlet pipe 76 is arranged axially of the shaft 74 for feed of blood into the housing 78 enclosing the impeller 72. The housing 78 also communicates with an outlet pipe 80 arranged tangentially thereto to receive and discharge blood impelled thereto by the impeller 72.

The inlet pipe 76, housing 78 and outlet pipe 80 may be constructed of any convenient rigid material, such as, rigid metal and/or rigid polymeric material while the impeller 72 may be constructed of any convenient rigid or flexible metal or polymeric material. As discussed in detail above with respect to the housing 12 and diaphragm 16 of the blood pump 10, the blood engaging surfaces of these members are porous and communicate with a subsurface network of pores, so that a tissue coating forms thereon.

DESCRIPTION OF ADDITIONAL STRUCTURE

The present invention also includes tubular members which access blood vessels either wholly subcutaneously or transcutaneously. Such vascular access tubes may be constructed or metal or rigid or flexible polymeric material.

The blood engaging portions of the tubes are formed of a composite of a dense coherent substrate and rigid porous coating which is adhered to the substrate.

When constructed of metal, the particles in the metal coating generally have a particle size of about −100 mesh, preferably −325 mesh and more preferably −500 mesh. The coating has a porosity of about 10 to about 50% by volume and the surface-coating interface and the coating itself have a shear strength of greater than about 1000 psi to ensure adequate structural strength.

The porous coating may have a thickness which varies widely up to about 500 microns, a thickness in the range of about 20 to about 300 microns being preferred.

EXAMPLE

An experimental model was developed to test for endothialization of porous metal coating when applied over the internal surface area of a conduit implanted to chronically surround flowing blood, analogous to the containment of flowing blood in an implantable blood pump.

Twelve stainless steel (316L) tubes or 5 cm length, 1.1 cm internal diameter and 1.2 cm external diameter were porous metal coated on the internal surface only to a coating thickness of about 150 microns with a 20 to 50 micron (+325 −500 mesh) particle size fraction. The scanning electron micrographs of FIGS. 3 and 4 show the form of the surface.

The twelve porous metal coated conduits were implanted in the descending thoracic aorta in dogs, which were chosen in a narrow weight range of 22 to 25 kg to provide a consistently close fit between the encircling aorta and the metal conduit within it. Under inflow occlusion, each conduit was introduced through an aortotomy immediately distal to the origin of the left subclavian artery. No postoperative anticoagulants were given.

Two dogs were sacrificed at each of two weeks, one month, two months, three months, six months and one year after implantation. At explant, each dog was anticoagulated with heparin (3 mg/kg), in order to eliminate any uncertainty about antemortem versus postmortem coagulation.

The blood was rinsed from each conduit in situ with isotonic saline and then the conduit was processed for scanning electron microscopy (SEM) and bisected longitudinally. One half of the specimen was retained for gross examination and the other half was divided into proximal, middle and distal thirds for SEM examination to determine the nature of the tissue response and its uniformity within the length of the conduit. In addition, gross and light microscopic examination of the kidneys and spleen for evidence of emboli was performed.

As a result of the above-noted examinations, it was observed that the porous metal surfaced aortic conduits were all patent and showed a progression in tissue response at the porous metal surfaces from a platelet-fibrin-erythrocyte-leukocyte meshwork at two weeks to a smooth surface lined by endothelial-like cells at six months and one year, in the form shown in the SEM of FIG. 5.

At one month, the process of organization of the initial laying down of blood cells in the interstices of the porous surface was well developed with fibroconnective tissue cells resembling fibroblasts evident on the blood-contacting surface. Between one and three months, there was more organization, with fibroblast-like cells becoming the dominant cell type. At six months the blood-contacting surface was uniformly endothelialized.

Gross and microscopic examination of the kidneys and spleen in each dog for thromboemboli was entirely negative.

These results demonstrate that under the conditions to be encountered in an implantable blood pump endothialization of a porous metal coating occurred and the incidence of thromboembolism was avoided.

SUMMARY OF DISCLOSURE

In summary of this disclosure, the present invention provides implantable artificial blood pumps which avoid prior art thromboembolic problems by inducing the formation of tissue on the blood-contacting surfaces thereof. Modifications are possible within the scope of the invention.

What I claim is:

1. A blood pump, comprising:
   A rigid housing having an integral wall, said housing being constructed of a rigid material substantially inert to blood,
   a resiliently flexible diaphragm located in said housing and defining a cavity with said internal wall, said diaphragm being constructed of resiliently flexible biocompatible polymeric material, said diaphragm being constructed to cyclically flex between contracted and expanded positions to vary the working volume of said cavity,
   means for effecting cyclical flexing of said diaphragm between said contracted and expanded positions,
   inlet means to said housing communication with said cavity and having first one-way valve means located therein permitting flow of blood into said cavity through said inlet means in response to an increase in the working volume of said cavity, and
   outlet means from said housing communicating with said cavity and having second one-way valve means located therein permitting flow of blood out of said cavity through said outlet means in response to a decrease in the working volume of said cavity,
   said internal wall of the rigid housing being composed of a single material of construction and consisting of a porous blood-engaging surface portion integral with a coherent substrate portion, said porous surface portion having a network of interconnected pores therein, a pore size of less than 200 microns, a porosity of about 10 to about 50% by volume and a thickness of up to about 500 microns,
   said surface portion being constituted by a plurality of particles which are integrally joined to each other at their points of contact with each other by the material of construction of said internal wall to define said network of interconnected pores and which are integrally joined to said coherent substrate portion by the material of construction of said internal wall.

2. The blood pump of claim 1 wherein said porous portion has a thickness of about 20 to about 300 microns and a pore size of less than about 50 microns.

3. The blood pump of claim 1 wherein said inlet means and outlet means are constituted by conduits interally formed with said rigid housing, and said inlet and outlet conduits each has an internal wall composed of a single material of construction and consisting of a porous blood-engaging surface portion integral with a coherent substrate, said porous surface having a network of interconnected pores therein and dimensions identical to those for the porous surface on said internal wall of the rigid housing.

4. The blood pump of claim 1 wherein said diaphragm has at least sufficient strength to withstand pulsatile arterial blood pressure of greater than about 300 mm Hg for at least one year, and said diaphragm consists of a resiliently-flexible coherent substrate and resiliently-flexible porous coating layer on the cavity side thereof adhered to the substrate layer and having a network of interconnected pores distributed therethrough, said porous coating having a pore size of less than about 200 microns, a porosity of about 10 to about 70% by volume and a thickness of less than about 500 microns.

5. The blood pump of claim 4 wherein said pore size is less than 50 microns and said coating has a thickness of about 20 to about 300 microns.

6. The blood pump of claim 4 wherein said diaphragm has a thickness of about 0.2 to about 1.0 mm.

7. A blood pump, comprising
   a rigid housing having a generally circularly cross-sectioned cavity, said housing being constructed of rigid material substantially inert to blood,
   inlet means coaxial with said housing and communicating with said cavity permitting flow of blood into said cavity through said inlet means,
   outlet means tangential to said housing and communicating with said cavity permitting flow of blood out of said cavity through said outlet means, and
   impeller means mounted in said cavity for rotation about an axis coaxial with said inlet means for impelling blood within said cavity from said inlet means to said outlet means, the internal wall of said cavity being composed of a single material of construction and consisting of a porous blood-engaging surface portion integral with a coherent substrate portion, said porous network portion having a network of interconnected pores therein, a pore size of less than 200 microns, a porosity of about 10 to about 50% by volume and a thickness of up to about 500 microns, said surface portion being constituted by a plurality of particles which are integrally joined to each other at their points of contact with each other by the material of construction of said internal wall to define said network of interconnected pores and which are integrally joined to said coherent substrate portion by the material of construction of said internal wall.

8. The blood pump of claim 7 wherein said porous portion has a thickness of about 20 to about 300 microns and a pore size of less than about 50 microns.

9. The blood pump of claim 7 wherein said inlet means and outlet means are constituted by conduits integrally formed with said rigid housing, and said inlet and outlet conduits are constructed identically to said internal wall of said cavity.

10. The blood pump of claim 1 or 7 wherein the outer surface of said rigid housing has a porous surface portion having a network of interconnected pores therein.

11. The blood pump of claim 1, 2, 3, 4, 5, 6, 7, 8 or 9 wherein said rigid housing is constructed of metal and said porous surface portion is constituted by a plurality of spherical metal particles integrally joined together with each other and to said coherent substrate portion.

12. The blood pump of claim 11 wherein said metal particles have a particle size selected from $-100 +325$ mesh, $-325 +500$ mesh and $-500$ mesh.

13. A blood pump diaphragm constructed of resiliently-flexible biocompatible polymeric material and comprising a planar sheet having at least sufficient strength to withstand pulsatile arterial blood pressure of greater than about 300 mm Hg in its physiological environment for at least 1 year, said sheet comprising a resiliently-flexible coherent polymeric substrate layer and a resiliently-flexible porous coating layer adhered to the substrate layer and adapted to engage blood and having a network of interconnected pores distributed therethrough, said porous coating layer consisting of particles of material joined together by the material of construction thereof, said porous coating having a pore size of less than about 200 microns, a porosity of about 10 to about 70% by volume and a thickness of less than about 500 microns.

14. The diaphragm of claim 13, wherein said pore size is less than about 50 microns and said coating has a thickness of about 20 to about 300 microns.

15. The diaphragm of claim 13 having a thickness of about 0.2 mm to about 1.0 mm.

* * * * *

(12) REEXAMINATION CERTIFICATE (4272nd)
United States Patent
MacGregor (10) Number: US 4,458,366 C1
(45) Certificate Issued: Feb. 20, 2001

(54) ARTIFICIAL IMPLANTABLE BLOOD PUMP

(75) Inventor: David C. MacGregor, 81 Wimbleton Rd., Islington, Ontario (CA)

(73) Assignee: David C. MacGregor, Islington (CA)

Reexamination Requests:
No. 90/004,044, Dec. 12, 1995
No. 90/004,253, May 28, 1996
No. 90/004,764, Sep. 29, 1997

Reexamination Certificate for:
Patent No.: 4,458,366
Issued: Jul. 10, 1984
Appl. No.: 06/405,763
Filed: Aug. 6, 1982

Related U.S. Application Data (63) Continuation of application No. 06/157,952, filed on Jun. 9, 1980, now abandoned, which is a continuation-in-part of application No. 05/824,296, filed on Aug. 15, 1977, now Pat. No. 4,280,514, which is a continuation-in-part of application No. 05/683,382, filed on May 5, 1976, now Pat. No. 4,101,984.

(51) Int. Cl.$^7$ ............................................. A61M 1/10
(52) U.S. Cl. ..................... 623/3.13; 623/3.16; 623/3.29; 128/899
(58) Field of Search ........................... 623/1, 12, 3, 3.16, 623/3.13, 3.29

(56) References Cited

U.S. PATENT DOCUMENTS

| | | |
|---|---|---|
| 3,182,335 | 5/1965 | Bolie . |
| 3,425,064 | 2/1969 | Carnevale et al. . |
| 3,478,695 | 11/1969 | Goranson et al. . |
| 3,505,987 | 4/1970 | Heilman et al. . |
| 3,513,486 | 5/1970 | Cotton de Bennetot et al. . |
| 3,518,702 | 7/1970 | La Russa . |
| 3,550,162 | 12/1970 | Huffman et al. . |
| 3,568,214 | 3/1971 | Goldschmied . |
| 3,604,016 | 9/1971 | Robinson et al. ..................... 623/3 |
| 3,608,088 | 9/1971 | Dorman et al. . |
| 3,641,591 | 2/1972 | Kolff ..................................... 623/3 |
| 3,647,324 | 3/1972 | Rafferty et al. . |
| 3,668,708 | 6/1972 | Tindal .................................. 623/3 |
| 3,685,059 | 8/1972 | Bokros et al. ....................... 623/3 |
| 3,733,616 | 5/1973 | Willis, Jr. ............................. 623/3 |
| 3,855,638 | 12/1974 | Pilliar ................................ 623/16 |
| 4,016,303 | 4/1977 | Poirier et al. ........................ 427/2 |

OTHER PUBLICATIONS

Akutsu, "Artificial Hearts: Available Types," in *Heart Substitutes*, ed. Albert Brest, pp. 165–182 (1966).
Akutsu, "Artificial Heart—Total Replacement and Partial Support," pp. 6–16 (1975).
Bernstein et al., "A Compact, Low Hemolysis, Non–Thrombogenic System for Non–Thoracotomy Prolonged Left Ventricular Bypass", Trans. Amer. Soc. Artif. Int. Organs, vol. XX, 1974, pp. 643–651.
Johnston et al., "Prolonged Pulsatile and Nonpulsatile LV Bypass with Centrifugal Pump", Trans. Amer. Soc. Artif. Int. Organs, vol. XXII, 1976, pp. 323–331.
Kolff, "Artificial Organs," pp. 4–11 (1976).
MacGregor et al., "Porous Metal Surface: A Radical New Concept in Prosthetic Heart Valve Design", Trans. Amer. Soc. Artif. Int. Organs, vol. XXII, 1976, pp. 646–653.
"Mechanical Devices to Assist the Failing Heart," Proceedings of a conference sponsored by the Committee on Trauma Division of Medical Sciences, National Academy of Sciences, National Research Council, Publication No. 1283, pp. 77–79 and 106–109 (1966).
Trans. Amer. Soc. Artif. Int. Organs, vol. XVI, 1970, pp. 416–418.
Trans. Amer. Soc. Artif. Int. Organs, vol. XIX, 1973, p. 264.
Welsh, R.P. et al., Surgical implants. "The role of Surface porosity in fixation to bone and acrylic.", J. Bone Joint Surg.[Am], 53:963, 1971.

*Primary Examiner*—Michael Milano (57) ABSTRACT

Implantable artificial blood pumps are described. The blood-contacting surfaces have pores therein which communicate with a subsurface of interconnected pores. This structure induces tissue formation thereon and avoidance of the incidence of thromboembolism.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *